United States Patent

Debry

[11] Patent Number: 5,911,756
[45] Date of Patent: Jun. 15, 1999

[54] INTRALARYNGEAL PROSTHESIS

[75] Inventor: Christian Max Debry, Paris, France

[73] Assignee: Novatech, Plan de Grasse, France

[21] Appl. No.: 08/876,245

[22] Filed: Jun. 16, 1997

[30]  Foreign Application Priority Data

Jun. 26, 1996 [FR] France ................................. 96 07921

[51] Int. Cl.⁶ .................................................. A61F 2/20
[52] U.S. Cl. ............................................................ 623/9
[58] Field of Search ............................ 623/9; 128/207.16

[56]  References Cited

U.S. PATENT DOCUMENTS 4,794,924  1/1989  Elichar .

FOREIGN PATENT DOCUMENTS 0 279 484   8/1988   European Pat. Off. .
2509605    7/1981   France .
WO 89/07916  9/1989   WIPO .

*Primary Examiner*—Mickey Yu
*Assistant Examiner*—John M. Black
*Attorney, Agent, or Firm*—Fisher, Christen & Sabol

[57]  ABSTRACT

A prosthesis (P1, P2) intended to remedy laryngeal dysfunction includes a tubular body (1) which is intended to be introduced into the larynx (8) and which, at one of its ends is shaped in a bevel (3) and which includes, on the one hand, an inclined closure face (4) and, on the other hand, lateral orifices (5) for communication between the inside of said tubular body (1) and the area outside of said tubular body (1).

9 Claims, 2 Drawing Sheets

INTRALARYNGEAL PROSTHESIS

BACKGROUND OF THE INVENTION

The present invention concerns an intralaryngeal prosthesis.

It is known that, during the act of swallowing, the principal function of the larynx is to close off the airways so as to protect them and prevent the bolus of food from passing into them instead of moving through the esophagus. This closure is effected by a neuromuscular reflex shutting the glottis, resulting from the adduction of muscle groups located at three levels (aryepiglottic, ventricular bands and vocal cords). Dysfunction at one of these levels leads to problems in swallowing, since the larynx can no longer guarantee correct closure of the airways, with the result that the bolus of food can pass into these. This of course has dramatic consequences for the patient.

To date, only a tracheotomy has been able to prevent the dramatic consequences of laryngeal dysfunction. This involves permanent provision of an inflated tracheal balloon closing off the trachea upstream of a cannula arranged in the tracheotomy orifice.

It will be appreciated, then, that the present treatment of laryngeal dysfunction is particularly severe and mutilating and results in very great discomfort for the patients. Moreover, there is a risk of the tracheal balloon leading to tracheal complications, such as necrosis or secondary stenosis.

SUMMARY OF THE INVENTION

The object of the present invention is therefore to overcome these disadvantages and to permit laryngeal dysfunction to be treated either without tracheotomy, or with tracheotomy but with no tracheal balloon, which, in both cases, increases patient comfort.

To this end, according to the invention, the prosthesis intended to remedy laryngeal dysfunction is distinguished by the fact that it includes a tubular body which is intended to be introduced into the larynx and which, at one of its ends is shaped in a bevel and which includes an inclined closure face and lateral orifices for communication between the inside of the tubular body and the area outside the tubular body.

Thus, when the prosthesis according to the present invention is in the intralaryngeal position, the inclined closure face directs the bolus of food from the mouth toward the esophagus, without any possibility of introduction into the airways. By contrast, by virtue of the lateral communication orifices, the circulation of air is not interrupted in the airways.

The tubular body can be flexible, semi-rigid or rigid.

The prosthesis is preferably made of a biocompatible material, for example silicone.

In a first embodiment, the inclined closure face is fixed and integral with the peripheral edge of the beveled end.

However, in an alternative embodiment, the inclined closure face is integral with the beveled end only at the extreme portion of the bevel.

Thus, in the latter case, the inclined closure face is hinged and forms a sort of flap which closes off the tubular body to a greater or lesser extent depending on the inspiration, expiration and/or swallowing.

The tubular body advantageously includes external projecting studs allowing said prosthesis to be fixed in position inside the larynx by means of the studs bearing against the inner wall thereof. To allow the prosthesis to take up its position easily at the level of the vocal cords, the end of the tubular body directed away from the bevel advantageously has a diameter which is smaller than at the bevel.

The lateral communication orifices are advantageously formed by indentations in the peripheral edge of the beveled end of the tubular body.

It will be noted that document FR-A-2 509 605 has already disclosed a total prosthesis intended to replace the entire larynx while at the same time ensuring swallowing and breathing via an upper route. This known prosthesis therefore constitutes an artificial larynx which by its very nature necessitates laryngectomy and tracheotomy.

This known artificial larynx includes, at its upper part, a cover of general conical shape which is provided with an orifice to which a flap is connected.

Thus, on the one hand, such a prosthesis is not suitable for treatment of laryngeal dysfunction and, on the other hand, necessarily consists of a plurality of different pieces made of different materials.

By contrast, the intralaryngeal prosthesis according to the present invention can consist of only two pieces, one being the tubular body and the other being the closure face, made of the same biocompatible material and bonded to one another, or of one single piece made of biocompatible material including the tubular body and the closure face.

BRIEF DESCRIPTION OF THE DRAWINGS

The figures in the attached drawing will make clear how the invention can be realized. In these figures, identical references designate similar elements.

DETAILED DESCRIPTION OF THE INVENTION

Figure 1:
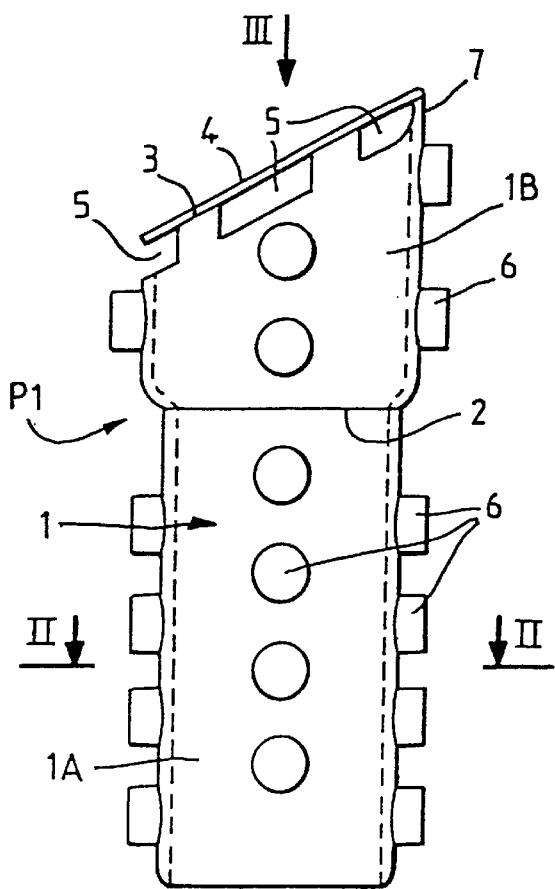
FIG. 1 is a side view of a first embodiment of the intralaryngeal prosthesis according to the present invention.
Figure 3:
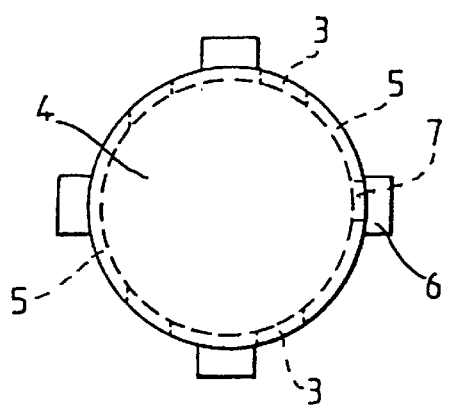
FIG. 3 is a plan view in the direction of the arrow III in FIG. 1.
Figure 2:
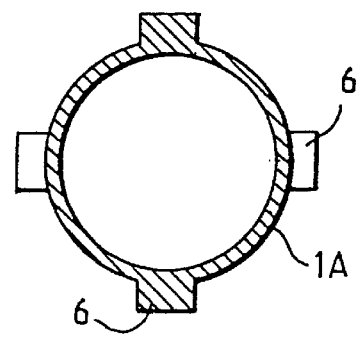
FIG. 2 is a cutaway view along the line II—II in FIG. 1.

The illustrative embodiment P1 of the intralaryngeal prosthesis according to the present invention, and represented in FIGS. 1, 2 and 3, includes a tubular body 1 whose lower part 1A has a smaller diameter than the upper part 1B, said parts 1A and 1B being joined to one another along a line 2.

Furthermore, the end of the upper part 1B directed away from the lower part 1A is shaped in a bevel 3 and is closed off by an inclined closure face 4 which is integral with the peripheral edge of the bevel 3.

Indentations 5 are cut in the bevel 3 and afford free gaseous communication between the inside of the tubular body 1 and the area outside the tubular body 1, at the upper part of the prosthesis. On the outer face of the tubular body 1 there are projecting studs 6.

The prosthesis P1 can be flexible and consist of two pieces of silicone bonded to one another by an appropriate adhesive, namely the tubular body 1 and the inclined closure face 4. It can also consist of a single piece made of silicone including the flexible tubular body 1 and the inclined closure face 4.

Figure 4:
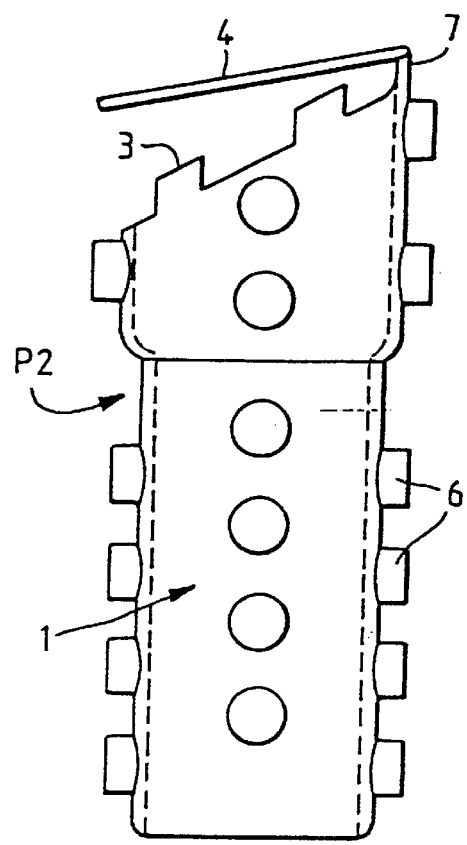
FIG. 4 is a side view of an alternative embodiment of the prosthesis according to the present invention.

The alternative embodiment P2 in FIG. 4 is essentially identical to the embodiment P1 in FIGS. 1 through 3. However, in the case of the prosthesis P2, the inclined closure face 4 is not integral with the whole of the peripheral edge of the bevel 3, but only with the extreme portion 7 of the bevel 3.

Thus, in this case, the inclined face 4 is hinged and can either bear against the peripheral edge of the bevel 3 or move away from the latter.

As has been mentioned above with regard to the embodiment P1, the embodiment P2 can consist of one or two pieces made of silicone.

Figure 5:
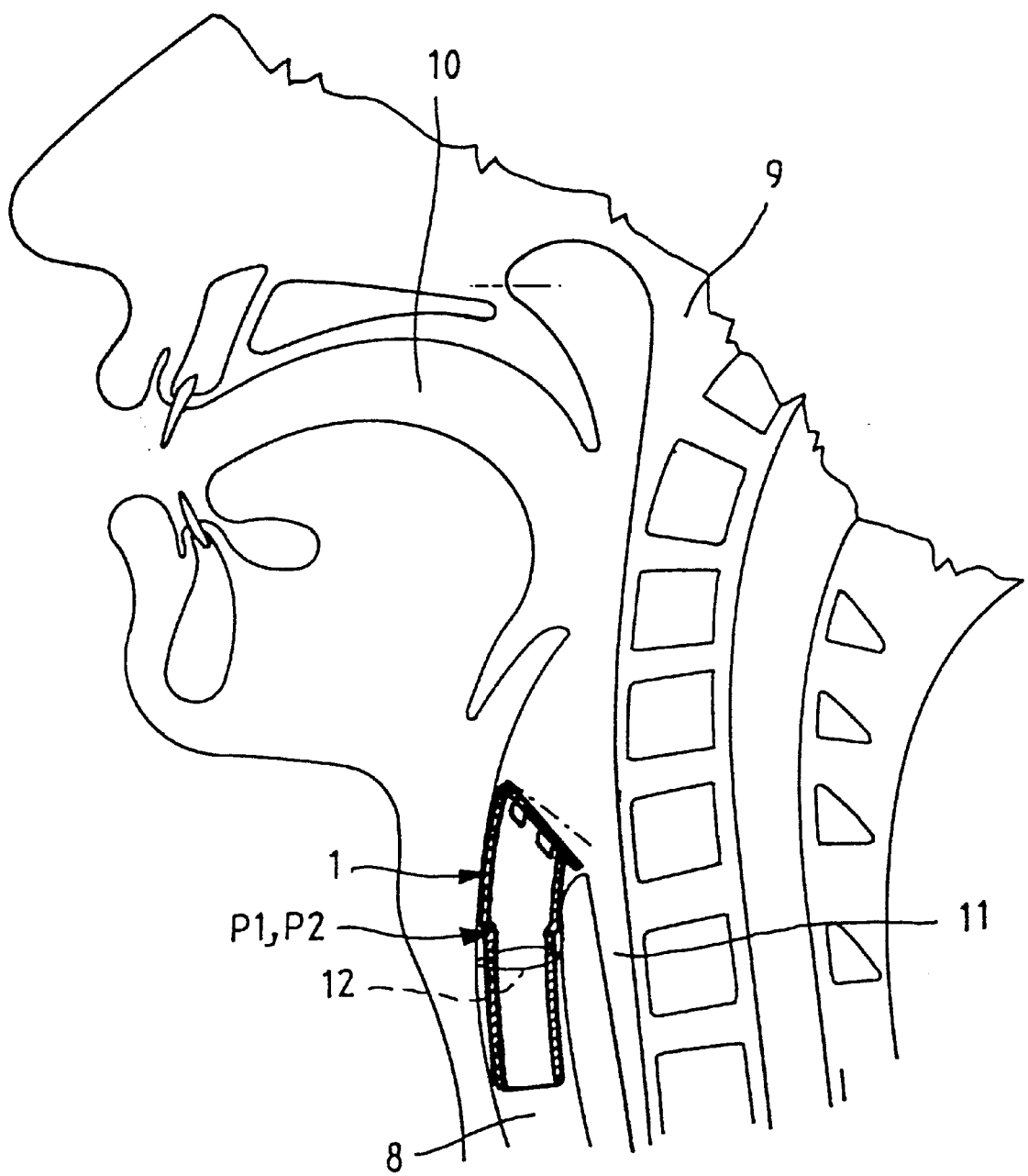
FIG. 5 illustrates the positioning of the prosthesis according to the invention inside the larynx of a patient.

By examining FIG. 5, in which the prosthesis P1 or P2 of the invention has been represented in place in the larynx 8 of a patient 9 presenting a dysfunction of the larynx, it will be readily appreciated that the bolus of food coming from the mouth 10 of said patient 9 cannot pass into the airways of the patient by way of the larynx. This is because the inclined closure face 4 closes off the tubular body 1 and directs this bolus of food toward the esophagus 11.

On the other hand, the prosthesis P1, P2 according to the present invention affords continuous air communication inside the airways by way of the tubular body 1, the indentations 5 and, where appropriate, through the opened end of the bevel 3 (in the case of embodiment P2).

The diameter of the upper part 1B of the tubular body 1 is of course adapted to the cross section of the upper part of the larynx 8, while the diameter of the lower part 1A of said tubular body 1 is smaller than that of the upper part 1B, so that this lower part 1A easily passes the vocal cords 12. The projecting studs 6 ensure the fastening of the prosthesis to the inner wall of the larynx 8.

I claim:

1. A laryngeal prosthesis adapted to remedy laryngeal dysfunction, comprising a tubular body having an inside and an upper portion and a lower portion, said lower portion of the tubular body being configured to be introduced into a larynx adjacent to vocal cords, the upper portion of the tubular body being a beveled end, the beveled end having an upper portion and a lower portion, the upper portion of the beveled end including a peripheral edge having an extreme portion, said beveled end of the tubular body being closed off by an inclined closure face which is integral with the extreme portion or all of the peripheral edge of the beveled end of the tubular body, the upper portion of the tubular body having a diameter adjacent to the lower portion of the tubular body and the lower portion of the tubular body having a diameter adjacent to the upper portion of the tubular body, and said peripheral edge including lateral orifices, said lateral orifices allowing for free gaseous communication between the inside of the tubular body and an area outside and above the tubular body when it is introduced into the larynx.

2. The prosthesis as claimed in claim 1, wherein said inclined closure face (4) is fixed and is integral with the peripheral edge of the beveled end (3).

3. The prosthesis as claimed in claim 1, wherein said inclined closure face (4) is hinged and is integral only with the extreme portion (7) of the beveled end (3).

4. The prosthesis as claimed in claim 1, wherein the prosthesis consists of two pieces which are made of biocompatible material and are joined together, namely said tubular body (1) and said inclined closure face (4).

5. The prosthesis as claimed in claim 1, wherein the prosthesis consists of one single piece made of biocompatible material, which forms said tubular body (1) and said inclined closure face (4).

6. The prosthesis as claimed in claim 1, wherein said prosthesis is made of silicone.

7. The prosthesis as claimed in claim 1, wherein said lateral orifices (5) are formed by indentations in the peripheral edge of the beveled end (3).

8. The prosthesis as claimed in claim 1, wherein said tubular body (1) includes external projecting studs (6) for holding said prosthesis inside the larynx.

9. The prosthesis as claimed in claim 1, wherein the diameter of the lower portion of the tubular body has a diameter which is smaller than the diameter of the upper portion of the tubular body.

* * * * *